US012633396B2

(12) United States Patent
Nakamura

(10) Patent No.: US 12,633,396 B2
(45) Date of Patent: May 19, 2026

(54) DOCUMENT CREATION SUPPORT APPARATUS, DOCUMENT CREATION SUPPORT METHOD, AND PROGRAM

(71) Applicant: FUJIFILM Corporation, Tokyo (JP)

(72) Inventor: Keigo Nakamura, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 301 days.

(21) Appl. No.: 18/332,762

(22) Filed: Jun. 12, 2023

(65) Prior Publication Data

US 2023/0317254 A1     Oct. 5, 2023

Related U.S. Application Data

(63) Continuation of application No. PCT/JP2021/046084, filed on Dec. 14, 2021.

(30) Foreign Application Priority Data

Jan. 20, 2021     (JP) ................................. 2021-007429

(51) Int. Cl.
*G16H 30/40*        (2018.01)
*A61B 5/00*         (2006.01)
(Continued)

(52) U.S. Cl.
CPC ............... *G16H 30/40* (2018.01); *A61B 5/00* (2013.01); *G06T 7/0012* (2013.01); *G06V 10/25* (2022.01); *G06V 10/764* (2022.01); *G16H 15/00* (2018.01); *G16H 50/20* (2018.01); *G16H 50/30* (2018.01); *G16H 50/70* (2018.01);
(Continued)

(58) Field of Classification Search
CPC ........ G16H 30/40; G16H 50/20; G16H 50/30; G16H 50/70; G16H 15/00; G06T 7/0012; G06T 2207/10081; G06T 2207/20084; G06T 2207/30096; G06V 10/25; G06V 10/764; G06V 2201/031; A61B 5/00
See application file for complete search history.

(56) References Cited

U.S. PATENT DOCUMENTS

| | | | |
|---|---|---|---|
| 10,755,413 B1 | 8/2020 | Putha et al. | |
| 2002/0131625 A1* | 9/2002 | Vining ................... | G16H 30/40 |
| | | | 382/128 |

(Continued)

FOREIGN PATENT DOCUMENTS

| | | |
|---|---|---|
| JP | 2008269041 | 11/2008 |
| JP | 2010029482 | 2/2010 |

(Continued)

OTHER PUBLICATIONS

"Search Report of Europe Counterpart Application", issued on Jun. 7, 2024, p. 1-p. 9.

(Continued)

*Primary Examiner* — Jennifer Mehmood
*Assistant Examiner* — Jose M Torres
(74) *Attorney, Agent, or Firm* — JCIPRNET

(57)     ABSTRACT

A document creation support apparatus includes at least one processor. The processor generates text describing a classification of a disease for at least one feature portion included in an image, and includes, in the text, a description regarding a relevant portion related to the classification of the disease described in the text.

6 Claims, 6 Drawing Sheets

10

(51) Int. Cl.

| | |
|---|---|
| *G06T 7/00* | (2017.01) |
| *G06V 10/25* | (2022.01) |
| *G06V 10/764* | (2022.01) |
| *G16H 15/00* | (2018.01) |
| *G16H 50/20* | (2018.01) |
| *G16H 50/30* | (2018.01) |
| *G16H 50/70* | (2018.01) |

(52) U.S. Cl.

CPC .............. *G06T 2207/10081* (2013.01); *G06T 2207/20084* (2013.01); *G06T 2207/30096* (2013.01); *G06V 2201/031* (2022.01)

(56) References Cited

U.S. PATENT DOCUMENTS

| | | | |
|---|---|---|---|
| 2007/0214013 | A1 | 9/2007 | Silverman |
| 2015/0262014 | A1 | 9/2015 | Iwamura et al. |
| 2015/0279061 | A1* | 10/2015 | Kutsuna ............... G06T 7/0012 382/131 |
| 2017/0337329 | A1* | 11/2017 | Liu ......................... A61B 6/463 |
| 2018/0046764 | A1 | 2/2018 | Katwala et al. |
| 2018/0060535 | A1* | 3/2018 | Reicher .................. G16H 50/30 |
| 2018/0114595 | A1* | 4/2018 | Stern ..................... G16H 80/00 |
| 2018/0253812 | A1* | 9/2018 | Iwase ..................... G16H 15/00 |
| 2018/0341751 | A1 | 11/2018 | Lyman et al. |
| 2018/0374246 | A1* | 12/2018 | Igarashi ............... A61B 5/0042 |
| 2019/0267120 | A1* | 8/2019 | Hirakawa .............. G16H 15/00 |
| 2020/0303062 | A1* | 9/2020 | Tao ......................... G06N 99/00 |
| 2020/0321100 | A1* | 10/2020 | Glottmann ............. G06N 3/044 |
| 2020/0402237 | A1* | 12/2020 | Song ...................... G16H 50/20 |
| 2020/0410678 | A1* | 12/2020 | Song .................... G06N 3/0442 |
| 2021/0042564 | A1* | 2/2021 | Xiao ..................... G06T 7/0012 |
| 2021/0335469 | A1* | 10/2021 | Xie ......................... G16H 10/60 |
| 2021/0343411 | A1* | 11/2021 | Zhang .................... G06N 3/042 |
| 2022/0028510 | A1 | 1/2022 | Nakamura et al. |
| 2022/0051771 | A1* | 2/2022 | Lyman ................. G06F 16/245 |
| 2022/0207722 | A1* | 6/2022 | Kim ...................... G06T 7/0012 |
| 2023/0024573 | A1* | 1/2023 | Lee ....................... G16H 15/00 |
| 2023/0067142 | A1* | 3/2023 | Yamazaki .............. G16H 50/70 |
| 2023/0154593 | A1* | 5/2023 | Gao ........................ G16H 30/40 382/181 |

FOREIGN PATENT DOCUMENTS

| | | |
|---|---|---|
| JP | 2015187845 | 10/2015 |
| JP | 2015191561 | 11/2015 |
| JP | 2017029411 | 2/2017 |
| JP | 2018077630 | 5/2018 |
| JP | 2020181288 | 11/2020 |
| WO | 2020209382 | 10/2020 |

OTHER PUBLICATIONS

Xiaosong Wang et al., "TieNet: Text-Image Embedding Network for Common Thorax Disease Classification and Reporting in Chest X-rays", arXiv:1801.04334v1 [cs.CV], Jan. 2018, pp. 1-16.

Guanxiong Liu et al., "Clinically Accurate Chest X-Ray Report Generation", arXiv:1904.02633, Jul. 2019, pp. 1-20.

Syed Qamrun Nisa et al., "Medical Image Analysis using Deep Learning: A Review", 2020 IEEE 7th International Conference on Engineering Technologies and Applied Sciences (ICETAS), Dec. 2020, pp. 1-3.

"International Search Report (Form PCT/ISA/210) of PCT/JP2021/ 046084", mailed on Mar. 8, 2022, with English translation thereof, pp. 1-6.

"Written Opinion of the International Searching Authority (Form PCT/ISA/237) of PCT/JP2021/046084", mailed on Mar. 8, 2022, with English translation thereof, pp. 1-8.

"Office Action of Japan Counterpart Application", issued on Jun. 17, 2025, with English translation thereof, pp. 1-5.

"Notice of Reasons for Refusal of Japan Counterpart Application", issued on Nov. 4, 2025, with English translation thereof, p. 1-p. 5.

\* cited by examiner

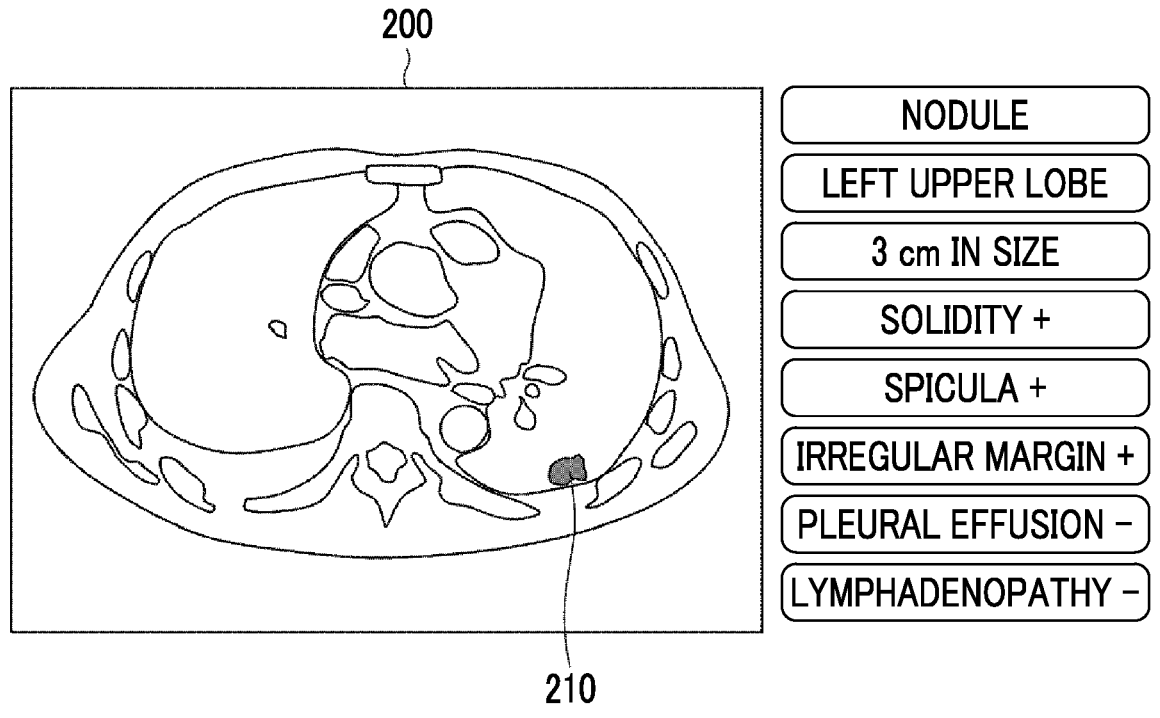

NODULE

LEFT UPPER LOBE 3 cm IN SIZE

SOLIDITY +

SPICULA +

IRREGULAR MARGIN +

PLEURAL EFFUSION −

LYMPHADENOPATHY −

| CLASSIFICATION OF DISEASE | FIRST RELEVANT PORTION | DETERMINATION ITEM FOR FIRST RELEVANT PORTION | SECOND RELEVANT PORTION | DETERMINATION ITEM FOR SECOND RELEVANT PORTION |
|---|---|---|---|---|
| NODULE | BETWEEN VISCERAL PLEURA AND PARIETAL PLEURA | PRESENCE OR ABSENCE OF PLEURAL EFFUSION | LYMPH NODE | PRESENCE OR ABSENCE OF LYMPHADENOPATHY |
| ATELECTASIS | - | - | - | - |
| ⋮ | ⋮ | ⋮ | ⋮ | ⋮ |

FIG. 8

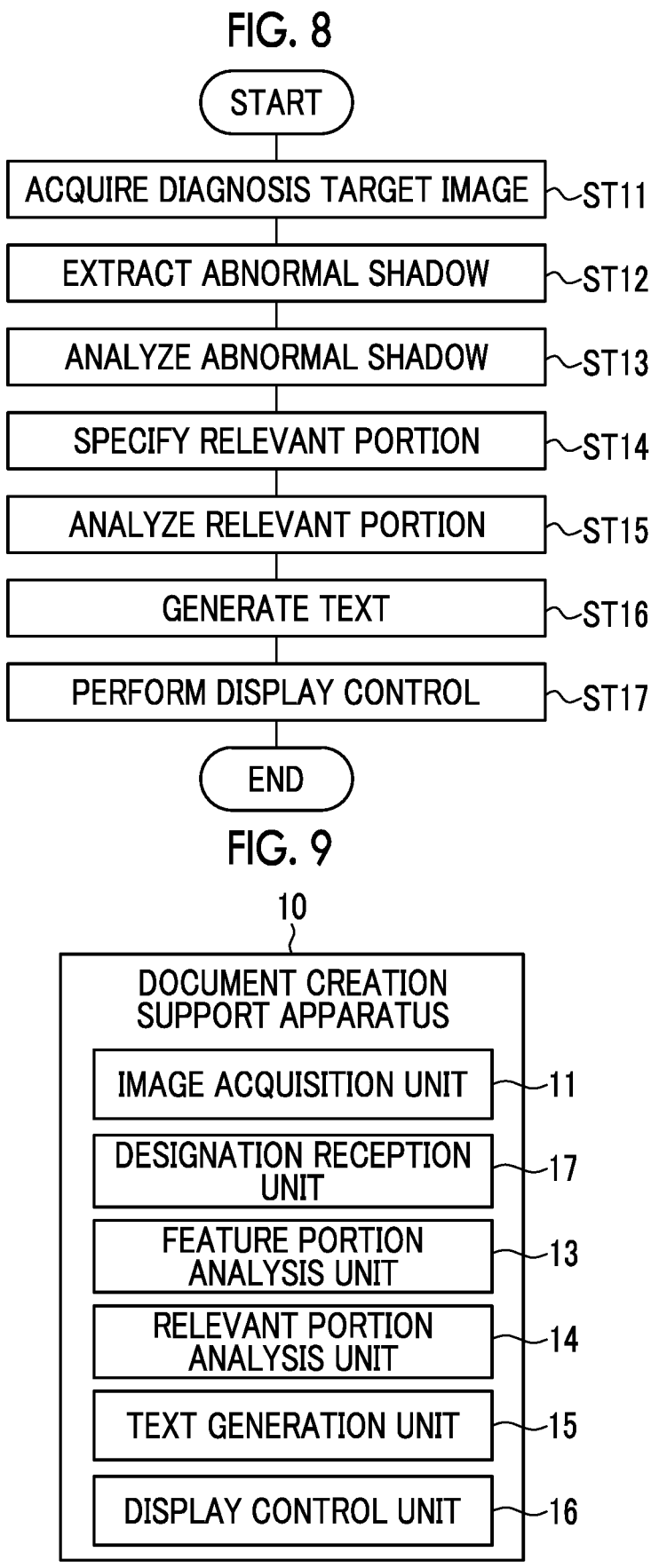

START

ACQUIRE DIAGNOSIS TARGET IMAGE — ST11

EXTRACT ABNORMAL SHADOW — ST12

ANALYZE ABNORMAL SHADOW — ST13

SPECIFY RELEVANT PORTION — ST14

ANALYZE RELEVANT PORTION — ST15

GENERATE TEXT — ST16

PERFORM DISPLAY CONTROL — ST17

END

DOCUMENT CREATION
SUPPORT APPARATUS

IMAGE ACQUISITION UNIT — 11

DESIGNATION RECEPTION
UNIT — 17

FEATURE PORTION
ANALYSIS UNIT — 13

RELEVANT PORTION
ANALYSIS UNIT — 14

TEXT GENERATION UNIT — 15

DISPLAY CONTROL UNIT — 16

DOCUMENT CREATION SUPPORT APPARATUS, DOCUMENT CREATION SUPPORT METHOD, AND PROGRAM

CROSS-REFERENCE TO RELATED APPLICATION

This application is a continuation application of International Application No. PCT/JP2021/046084, filed Dec. 14, 2021, the disclosure of which is incorporated herein by reference in its entirety. Further, this application claims priority from Japanese Patent Application No. 2021-007429 filed on Jan. 20, 2021, the disclosures of which is incorporated herein by reference in its entirety.

BACKGROUND

1. Technical Field

Disclosed technologies relate to a document creation support apparatus, a document creation support method, and a program.

2. Description of the Related Art

The following technologies are known as technologies related to a document creation support apparatus that creates text that can be applied to documents such as interpretation reports based on medical images. For example, JP2017-29411A describes a medical document creation apparatus that specifies attribute information related to the attribute information acquired in response to a user operation, collects finding information including the specified attribute information, and arranges and displays the collected finding information on a display unit.

JP2020-181288A describes a medical information processing apparatus comprising a reception unit that receives selection of a target part or a target disease, an extraction unit that extracts a past first event corresponding to the selected target part or target disease and a past second event corresponding to a part or disease related to the target part or target disease, and a display control unit that maps and displays the first event and the second event on a schema.

SUMMARY

It is assumed that an interpretation report created based on a medical image includes a description of the disease found in the medical image. Depending on the classification of the disease, it may be preferable to note that another disease may co-occur in a part other than the onset part of the disease. For example, in a case where a lung nodule is found in the medical image, it is preferable to note that pleural effusion may co-occur. In this case, it is preferable that the interpretation report includes not only the description of the lung nodule but also the description of the pleural effusion.

The disclosed technology has been made in view of the above points, and an object thereof is to include, in automatic generation of text based on an image, in the text, a description of a portion other than the main onset portion of a disease described in the text.

According to an aspect of the disclosed technology, there is provided a document creation support apparatus comprising at least one processor. The processor generates text describing a classification of a disease for at least one feature portion included in an image, and includes, in the text, a description regarding a relevant portion related to the classification of the disease described in the text.

The processor may include, in the text, the description regarding the relevant portion in a case where the classification of the disease described in the text is a specific classification. The processor may include, in the text, the description regarding the relevant portion in a case where the classification of the disease described in the text is malignant. The processor may receive a designation of the feature portion, and include, in the text, the description regarding the relevant portion related to the classification of the disease corresponding to the designated feature portion.

According to another aspect of the disclosed technology, there is provided a document creation support method in which at least one processor included in an information processing apparatus executes processing of: generating text describing a classification of a disease for at least one feature portion included in an image; and including, in the text, a description regarding a relevant portion related to the classification of the disease described in the text.

According to another aspect of the disclosed technology, there is provided a program for causing at least one processor included in an information processing apparatus to execute processing of: generating text describing a classification of a disease for at least one feature portion included in an image; and including, in the text, a description regarding a relevant portion related to the classification of the disease described in the text.

According to the aspects of the disclosed technology, it is possible to include, in automatic generation of text based on an image, in the text, a description of a portion other than the main onset portion of a disease described in the text.

BRIEF DESCRIPTION OF THE DRAWINGS

Exemplary embodiments according to the technique of the present disclosure will be described in detail based on the following figures, wherein:

FIG. 4 is a diagram for describing a function of the document creation support apparatus according to an embodiment of the disclosed technology;

FIG. 5 is a diagram showing an example of a relevant portion table according to an embodiment of the disclosed technology;

FIG. 8 is a flowchart showing an example of a flow of a document creation support process according to an embodiment of the disclosed technology; and FIG. 9 is a functional block diagram showing an example of a functional configuration of the document creation support apparatus according to an embodiment of the disclosed technology.

DETAILED DESCRIPTION

Figure 1:
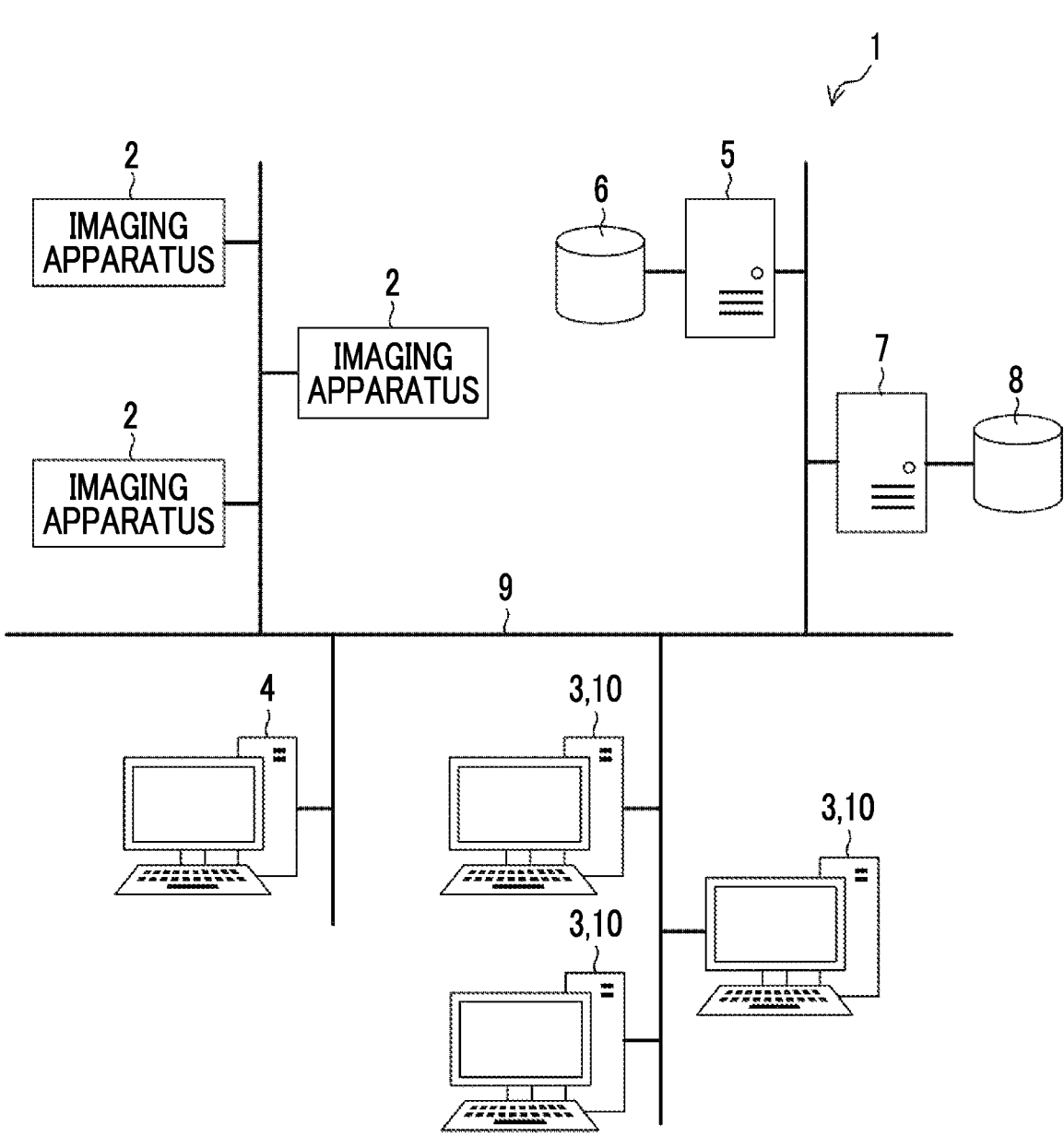
FIG. 1 is a diagram showing a schematic configuration of a medical information system according to an embodiment of the disclosed technology.

Hereinafter, embodiments of the disclosed technology will be described with reference to the drawings. In each drawing, substantially the same or equivalent components or portions are designated by the same reference numerals.

First Embodiment

FIG. 1 is a diagram showing a schematic configuration of a medical information system 1 to which a document creation support apparatus according to an embodiment of the disclosed technology is applied. The medical information system 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

In the medical information system 1, a plurality of imaging apparatuses 2, a plurality of interpretation workstations (WS) 3 that are interpretation terminals, a medical department workstation (WS) 4, an image server 5, an image database 6, an interpretation report server 7, and an interpretation report database 8 are communicably connected to each other through a wired or wireless network 9.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 9 or in a network storage in a state in which it can be accessed from the outside, and is downloaded to and installed on the computer in response to a request.

The imaging apparatus 2 is an apparatus that generates a medical image showing a diagnosis target part of the subject by imaging the diagnosis target part. The imaging apparatus 2 may be, for example, a simple X-ray imaging apparatus, a CT apparatus, an MRI apparatus, a positron emission tomography (PET) apparatus, and the like. A medical image generated by the imaging apparatus 2 is transmitted to the image server 5 and is saved therein.

The medical department WS 4 is a computer used by a doctor in a medical department to observe a medical image in detail, view an interpretation report, create an electronic medical record, and the like, and includes a processing apparatus, a display apparatus such as a display, and an input apparatus such as a keyboard and a mouse. In the medical department WS 4, each process such as creating a medical record (electronic medical record) of a patient, requesting to view an image from the image server 5, displaying a medical image received from the image server 5, automatically detecting or highlighting suspected disease regions in the medical image, requesting to view an interpretation report from the interpretation report server 7, and displaying the interpretation report received from the interpretation report server 7 is performed by executing a software program for each process.

The image server 5 is a general-purpose computer on which a software program that provides a function of a database management system (DBMS) is installed. The image server 5 comprises the image database 6 including a storage. The image database 6 may be a hard disk apparatus connected to the image server 5 by a data bus, or may be a disk apparatus connected to a storage area network (SAN) or a network attached storage (NAS) connected to the network 9. In a case where the image server 5 receives a request to register a medical image from the imaging apparatus 2, the image server 5 prepares the medical image in a format for a database and registers the medical image in the image database 6.

Image data of the medical image acquired by the imaging apparatus 2 and accessory information attached to the image data are registered in the image database 6. The accessory information includes, for example, an image identification (ID) for identifying each medical image, a patient ID for identifying a patient who is a subject, an examination ID for identifying an examination content, a unique ID (UID: unique identification) allocated for each medical image, examination date and examination time at which a medical image is generated, the type of imaging apparatus used in an examination for acquiring a medical image, patient information such as the name, age, and gender of a patient, an examination part (imaging part), imaging information (an imaging protocol, an imaging sequence, an imaging method, imaging conditions, the presence or absence of the use of a contrast medium, and the like), and information such as a series number or a collection number when a plurality of medical images are acquired in one examination. In addition, in a case where a viewing request from the interpretation WS 3 is received through the network 9, the image server 5 searches for a medical image registered in the image database 6 and transmits the searched for medical image to the interpretation WS 3 that is a request source.

The interpretation report server 7 incorporates a software program for providing a function of a database management system to a general-purpose computer. In a case where the interpretation report server 7 receives a request to register an interpretation report from the interpretation WS 3, the interpretation report server 7 prepares the interpretation report in a format for a database and registers the interpretation report in the interpretation report database 8. Further, in a case where the request to search for the interpretation report is received, the interpretation report is searched for from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, findings, and confidence of the findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the Internet or a dedicated line. In any case, it is preferable that the network 9 has a configuration capable of realizing high-speed transmission of medical images such as an optical network.

In the interpretation WS 3, each process such as requesting to view a medical image from the image server 5, various kinds of image processing on the medical image received from the image server 5, displaying the medical image, an analysis process on the medical image, highlighting the medical image based on the analysis result, creating the interpretation report based on the analysis result, supporting the creation of an interpretation report, requesting to register and view the interpretation report from the interpretation report server 7, and displaying the interpretation report received from the interpretation report server 7 is performed by executing a software program for each process. The interpretation WS 3 encompasses a document creation support apparatus 10 to be described later, and in the above processes, processes other than those performed by the document creation support apparatus 10 are performed by a well-known software program, and therefore the detailed description thereof will be omitted here. In addition, processes other than the processes performed by the document creation support apparatus 10 may not be performed in the interpretation WS 3, and a computer that performs the processes may be separately connected to the network 9, and in response to a processing request from the interpretation WS 3, the requested process may be performed by the computer. Hereinafter, the document creation support apparatus 10 encompassed in the interpretation WS 3 will be described in detail.

Figure 2:
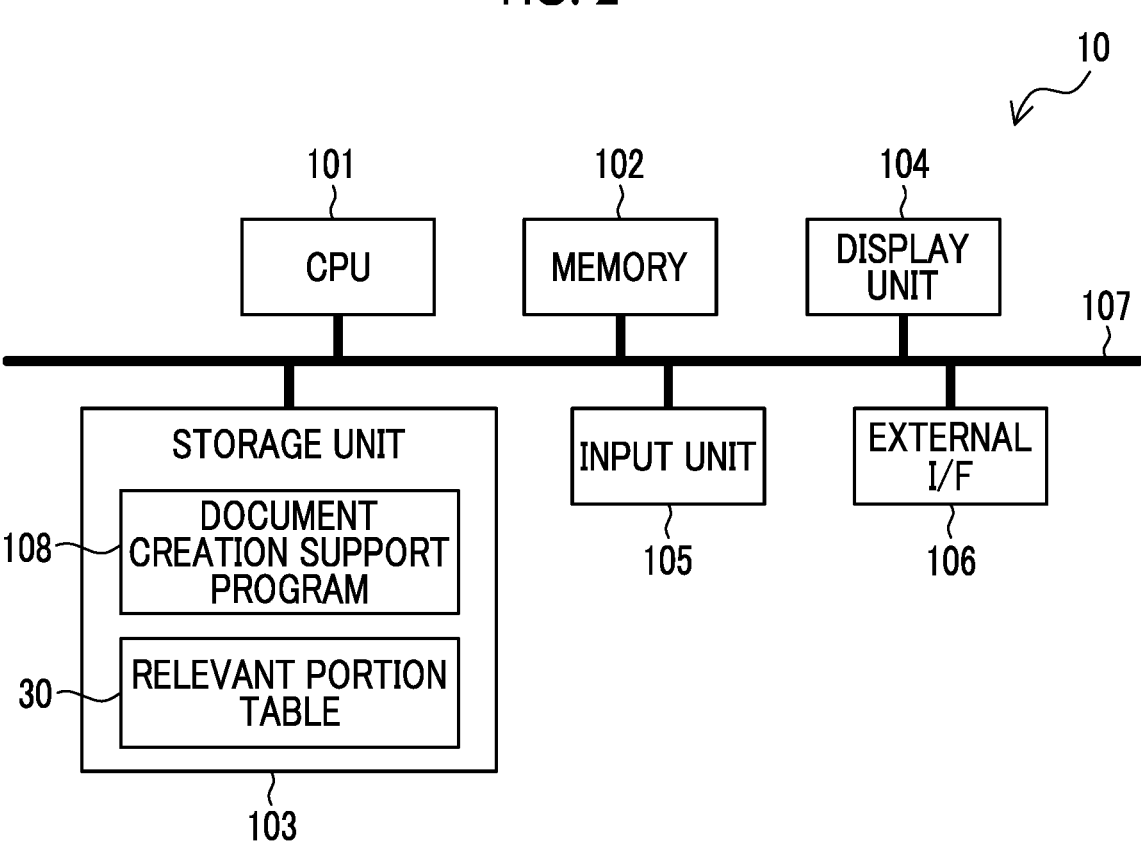
FIG. 2 is a diagram showing an example of a hardware configuration of a document creation support apparatus according to an embodiment of the disclosed technology.

FIG. 2 is a diagram showing an example of the hardware configuration of the document creation support apparatus 10. The document creation support apparatus 10 includes a central processing unit (CPU) 101, a memory 102, a storage unit 103, a display unit 104 consisting of a display device such as a liquid crystal display, an input unit 105 consisting of an input device such as a keyboard and a mouse, and an external interface (I/F) 106. The input unit 105 may be provided with a microphone that receives voice input. The CPU 101, the memory 102, the storage unit 103, the display unit 104, the input unit 105, and the external I/F 106 are connected to a bus 107. The document creation support apparatus 10 is connected to the network 9 of the medical information system 1 via the external I/F 106. The CPU 101 is an example of a processor in the disclosed technology.

The storage unit 103 is realized by a non-volatile storage medium such as a hard disk drive (HDD), a solid state drive (SSD), a flash memory, or the like. The storage unit 103 stores a document creation support program 108 and a relevant portion table 30 which will be described later. The document creation support program 108 is recorded on a recording medium such as a DVD or a CD-ROM, and distributed, and is installed on the document creation support apparatus 10 from the recording medium. Alternatively, the document creation support program 108 is stored in a storage apparatus of a server computer connected to the network or in a network storage in a state in which it can be accessed from the outside, and is downloaded to and installed on the document creation support apparatus 10 in response to a request. The CPU 101 reads out the document creation support program 108 from the storage unit 103, loads the read document creation support program 108 into the memory 102, and executes the loaded document creation support program 108.

Figure 3:
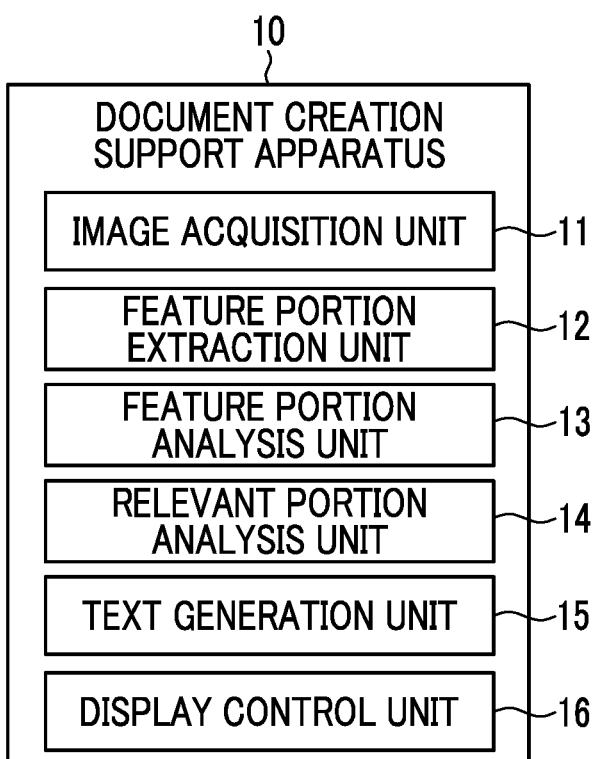
FIG. 3 is a functional block diagram showing an example of a functional configuration of the document creation support apparatus according to an embodiment of the disclosed technology.

FIG. 3 is a functional block diagram showing an example of the functional configuration of the document creation support apparatus 10. The document creation support apparatus 10 includes an image acquisition unit 11, a feature portion extraction unit 12, a feature portion analysis unit 13, a relevant portion analysis unit 14, a text generation unit 15, and a display control unit 16. The document creation support apparatus 10 functions as the image acquisition unit 11, the feature portion extraction unit 12, the feature portion analysis unit 13, the relevant portion analysis unit 14, the text generation unit 15, and the display control unit 16 by executing the document creation support program 108 by the CPU 101.

The image acquisition unit 11 acquires a medical image to be diagnosed (hereinafter referred to as a diagnosis target image). The diagnosis target image is saved in the image database 6, is transmitted from the image database 6 to the document creation support apparatus 10 in response to a request from the document creation support apparatus 10 (interpretation workstation 3), and is saved in the storage unit 103. The image acquisition unit 11 acquires the diagnosis target image saved in the storage unit 103. The image acquisition unit 11 may directly acquire the diagnosis target image saved in the image database 6 from the image database 6. In the following, a case where the diagnosis target image is a chest CT image will be described as an example.

The feature portion extraction unit 12 extracts a shadow where a disease such as a nodule or tumor is suspected (hereinafter referred to as an abnormal shadow) as a feature portion from the diagnosis target image acquired by the image acquisition unit 11. The feature portion extraction unit 12 may extract an abnormal shadow using, for example, a trained model trained by machine learning such as deep learning. The above-mentioned trained model is trained by machine learning using, for example, a plurality of combinations of a medical image including an abnormal shadow and information specifying a region in the image in which the abnormal shadow is present as training data. The above-mentioned trained model receives a medical image as an input and outputs a result of specifying an abnormal shadow region in the medical image. FIG. 4 shows an example in which an abnormal shadow 210 is extracted from a diagnosis target image 200.

The feature portion analysis unit 13 analyzes an abnormal shadow extracted from the diagnosis target image and specifies the classification of a disease corresponding to the abnormal shadow. The classification of a disease includes, for example, disease names and diagnosis names such as nodules, hemangiomas, cysts, lymphadenopathy, pleural effusion, and hamartoma, and also includes the classification of whether the disease is benign or malignant (cancer). The feature portion analysis unit 13 may specify the classification of a disease using, for example, a trained model trained by machine learning such as deep learning. The above-mentioned trained model is trained by machine learning using, for example, training data in which a medical image including an abnormal shadow is given the classification of a disease corresponding to the abnormal shadow as a correct label. The above-mentioned trained model receives a medical image as an input and outputs a classification of a disease corresponding to an abnormal shadow included in the medical image.

In addition, the feature portion analysis unit 13 analyzes the abnormal shadow extracted by the feature portion extraction unit 12 to specify the properties of the abnormal shadow for each of a plurality of predetermined property items. Examples of the property items specified for the abnormal shadow include the position, the size, the presence or absence of spicula, the presence or absence of an irregular margin, the presence or absence of solidity, the presence or absence of partial solidity, the presence or absence of pleural invagination, and the like in the corresponding abnormal shadow.

The feature portion analysis unit 13 may specify the property of an abnormal shadow using, for example, a trained model trained by machine learning such as deep learning. The above-mentioned trained model is trained by machine learning using, for example, a plurality of combinations of a medical image including an abnormal shadow and a property label representing the property of the abnormal shadow as training data. The above-mentioned trained model receives a medical image as an input, and outputs a property score derived for each property item in the abnormal shadow included in the medical image. The property score is a score indicating the prominence of the property for the property item. The property score takes a value of 0 or more and 1 or less, for example, and the larger the value of the property score is, the more pronounced the property is.

For example, in a case where the property score for "the presence or absence of spicula", which is one of the property items of an abnormal shadow, is, for example, 0.5 or more, the feature portion analysis unit 13 specifies that the property for "the presence or absence of spicula" of the corresponding abnormal shadow is "with spicula (positive)", and in a case where the property score for "the presence or absence of spicula" is less than, for example, 0.5, the feature portion analysis unit 13 specifies that the property for the presence or absence of spicula of the corresponding abnormal shadow is "no spicula (negative)". The threshold value 0.5 used for property determination is merely an example, and is set to an appropriate value for each property item.

FIG. 4 shows an example in which "nodule" is specified as a classification of a disease corresponding to the abnormal shadow 210 extracted from the diagnosis target image 200, and "left upper lobe", "3 cm in size", "solidity+", "spicula+", and "irregular margin+" are specified as the property of the abnormal shadow 210. The "+" notation in the specified property indicates that the property is positive.

The relevant portion analysis unit 14 specifies a relevant portion related to the classification of the disease specified by the feature portion analysis unit 13, and makes a determination on a predetermined determination item for the specified relevant portion. The relevant portion is a portion in the diagnosis target image in which the classification of another disease (for example, pleural effusion) that is expected to occur together with the classification of a disease (for example, nodule) corresponding to the abnormal shadow (feature portion) may occur. The relevant portion analysis unit 14 refers to a relevant portion table 30 stored in the storage unit 103 in specifying the relevant portion. The relevant portion table 30 records, for each classification of diseases, the relevant portions related to the classification in association with each other. The relevant portion table 30 may be created based on knowledge obtained from past cases.

FIG. 5 is an example of the relevant portion table 30. The relevant portion table 30 is stored in the storage unit 103. For example, "nodule", which is one of the classification of the disease, is expected to occur together with "pleural effusion" and "lymphadenopathy". Therefore, in the relevant portion table 30, the "nodule" is associated with "an area between the visceral pleura and the parietal pleura" where "pleural effusion" can occur as a first relevant portion, and is associated with the "lymph node" where "lymphadenopathy" can occur as a second relevant portion. Further, in the relevant portion table 30, the "presence or absence of pleural effusion" is associated as a determination item for the first relevant portion, and the "presence or absence of lymphadenopathy" is associated as a determination item for the second relevant portion.

In a case where the classification of the disease specified by the feature portion analysis unit 13 is "nodule" for the abnormal shadow, the relevant portion analysis unit 14 specifies "an area between the visceral pleura and the parietal pleura" as the first relevant portion based on the relevant portion table 30, and determines the "presence or absence of pleural effusion" for the first relevant portion. Further, the relevant portion analysis unit 14 specifies the "lymph node" as the second relevant portion based on the relevant portion table 30, and determines the "presence or absence of lymphadenopathy" for the second relevant portion. FIG. 4 shows an example in which "pleural effusion–" was derived as the determination result for the first relevant portion and "lymphadenopathy–" was derived as the determination result for the second relevant portion. The "–" notation in the derived determination result indicates that the findings are negative. In a case where the relevant portion analysis unit 14 makes a determination on the relevant portion, an image different from the diagnosis target image used for the extraction and analysis of the abnormal shadow may be used. For example, the relevant portion may be determined using a chest CT image of a tomogram different from the tomogram on which the abnormal shadow was extracted and analyzed. Depending on the classification of the disease, there may be no relevant portion to be associated. For example, for "atelectasis", since there is no other disease that is expected to occur together with atelectasis, the field of the relevant portion associated with "atelectasis" in the relevant portion table 30 shown in FIG. 5 is left blank.

The text generation unit 15 generates text describing the classification of the disease specified by the feature portion analysis unit 13 for the abnormal shadow extracted by the feature portion extraction unit 12. The text may include a description regarding the property of the abnormal shadow specified by the feature portion analysis unit 13. In addition, the text generation unit 15 includes, in the text, a description regarding the relevant portion related to the classification of the disease described in the text. The text generation unit 15 generates a description regarding the relevant portion based on the determination result for the relevant portion derived by the relevant portion analysis unit 14.

In order to describe the processing by the text generation unit 15, the following case is assumed as an example. As illustrated in FIG. 4, it is assumed that the feature portion analysis unit 13 specifies "nodule" as a classification of a disease corresponding to the abnormal shadow 210 extracted from the diagnosis target image 200, and specifies "left upper lobe", "3 cm in size", "solidity+", "spicula+", and "irregular margin+" as the property of the abnormal shadow 210. Further, a case is assumed in which the relevant portion analysis unit 14 determines that "there is no pleural effusion" in the "between the visceral pleura and the parietal pleura" as the first relevant portion related to the "nodule", and determines that "there is no lymphadenopathy" in the "lymph node" as the second relevant portion related to the "nodule". In this case, the text generation unit 15 generates, as an example, the text "Solid nodule of 3 cm in size is found in the left upper lobe. It is accompanied by spicula and has an irregular margin. No pleural effusion is found. No lymphadenopathy is found." That is, the text generation unit 15 generates the text including a description "nodule" as the description regarding the classification of the disease corresponding to the abnormal shadow, and descriptions "No pleural effusion is found" and "No lymphadenopathy is found" as the descriptions regarding the relevant portion related to the "nodule".

Figure 6:
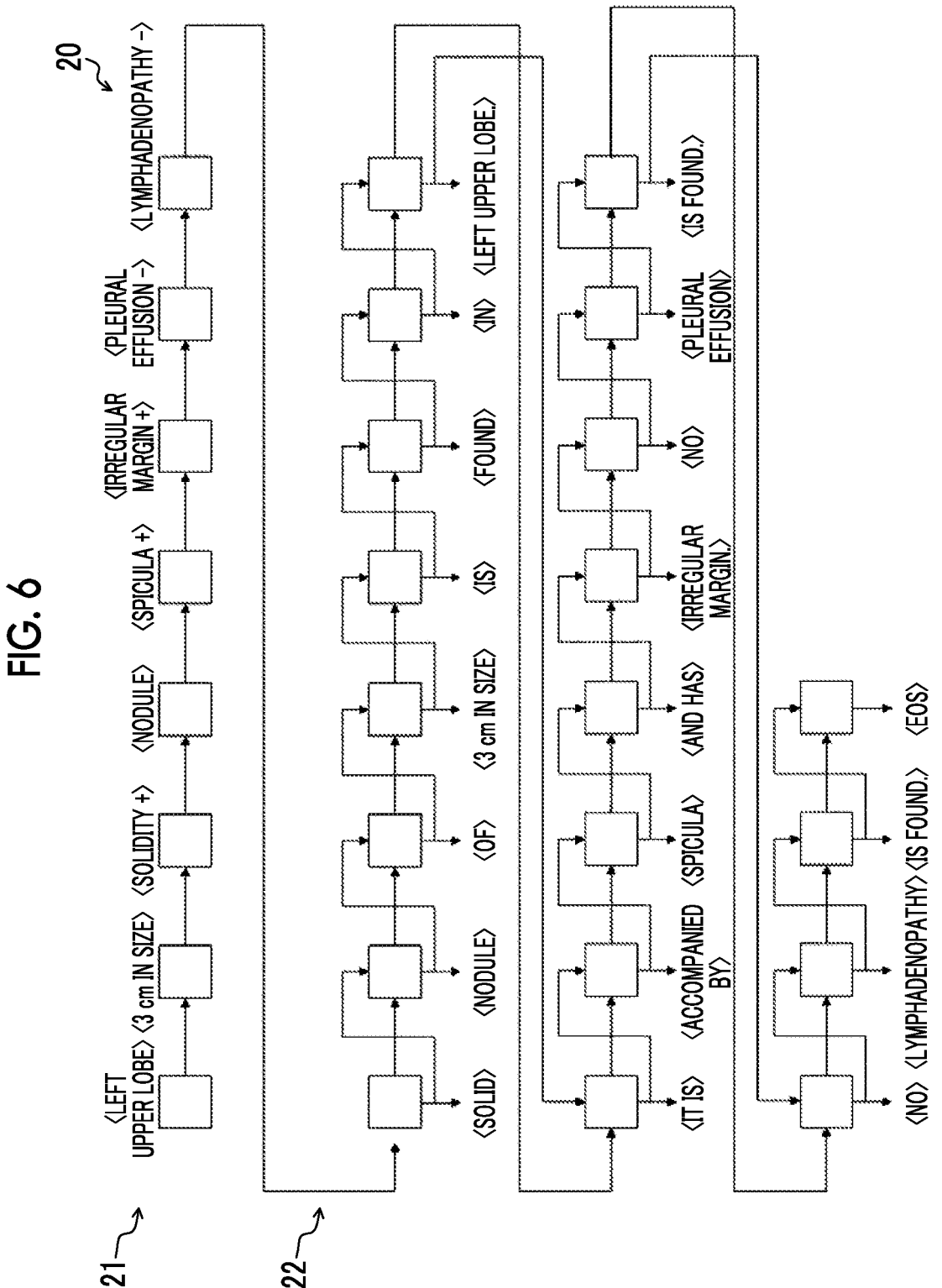
FIG. 6 is a diagram schematically showing an example of a configuration of a recurrent neural network constituting a text generation unit according to an embodiment of the disclosed technology.

The text generation unit 15 includes a recurrent neural network trained to create text from input words. FIG. 6 is a diagram schematically showing a configuration of a recurrent neural network. As shown in FIG. 6, a recurrent neural network 20 includes an encoder 21 and a decoder 22. In the encoder 21, characters corresponding to the classification and properties of the disease for the abnormal shadow (feature portion) specified by the feature portion analysis unit 13 and the determination result for the relevant portion derived by the relevant portion analysis unit 14 are input. FIG. 6 illustrates a case where "left upper lobe", "3 cm in size", "solidity+", "nodule", "spicula+", "irregular margin+", "pleural effusion−", and "lymphadenopathy−" are input to the encoder 21. The decoder 22 has been trained to convert words input to the encoder 21 into sentences, and from the above input words, the text "Solid nodule of 3 cm in size is found in the left upper lobe. It is accompanied by spicula and has an irregular margin. No pleural effusion is found. No lymphadenopathy is found." is generated. In FIG. 6, "EOS" indicates the end of the sentence (end of sentence).

Figure 7:
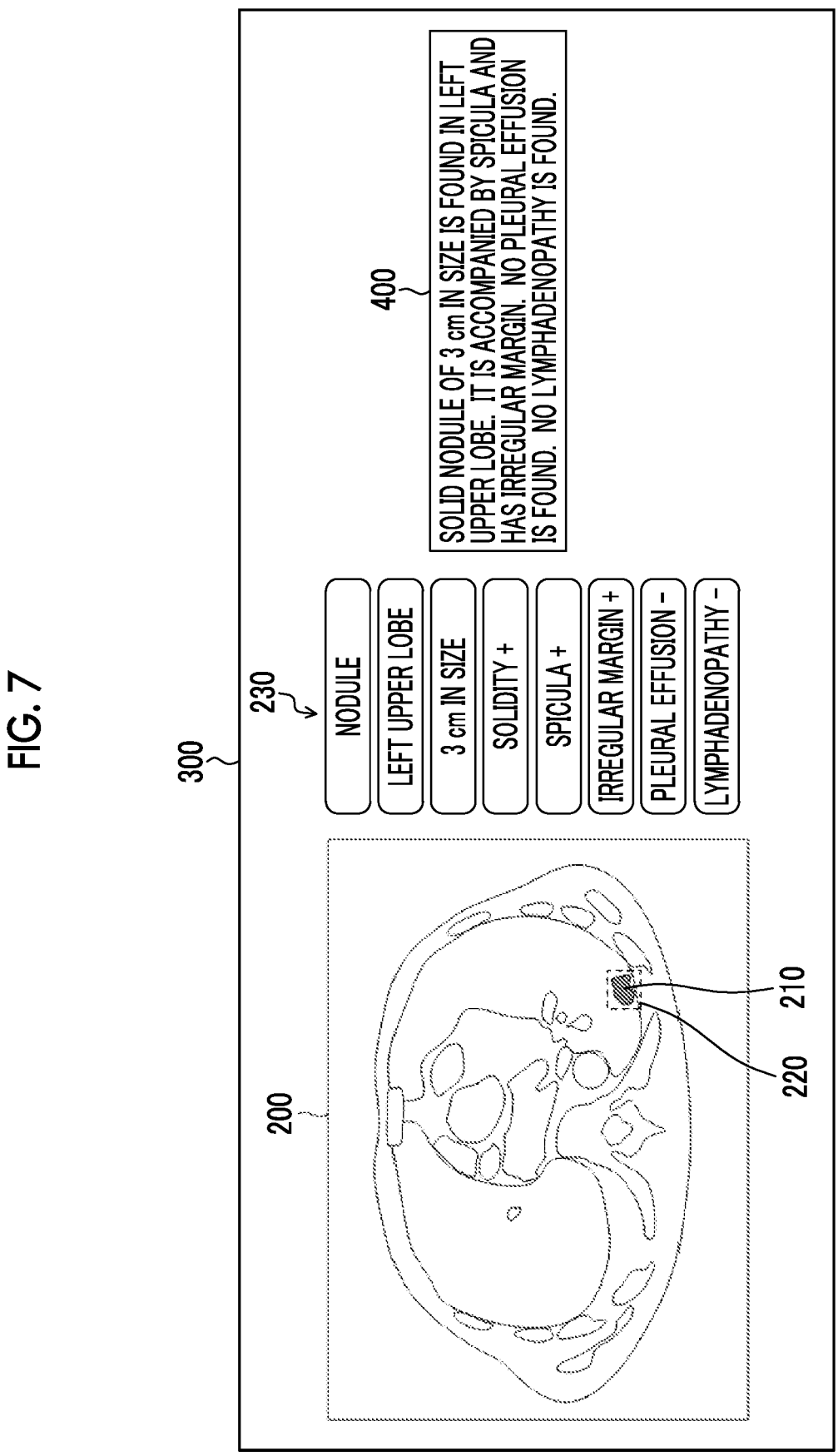
FIG. 7 is a diagram showing an example of a display mode of information displayed on a display screen according to an embodiment of the disclosed technology.

The display control unit 16 performs control such that the text generated by the text generation unit 15 is displayed on the display unit 104. FIG. 7 is a diagram showing an example of a display mode of information displayed on a display screen 300 of the display unit 104 under the control of the display control unit 16. As shown in FIG. 7, text 400 generated by the text generation unit 15 is displayed on the display screen 300. In addition, the diagnosis target image 200 including the abnormal shadow 210 used in generating the text 400 is displayed on the display screen 300. The diagnosis target image 200 may be provided with a mark 220 indicating the position of the abnormal shadow 210. Further, on the display screen 300, a label (icon) 230 indicating a determination result derived for the classification and properties of the disease and the relevant portion, in which the abnormal shadow 210 is specified, is displayed.

In the following, the operation of the document creation support apparatus 10 will be described. FIG. 8 is a flowchart showing an example of a flow of a document creation support process performed by the CPU 101 executing the document creation support program 108. The document creation support program 108 is executed, for example, in a case where an instruction to start execution is input by a user via the input unit 105. It is assumed that the diagnosis target image is downloaded from the image server 5 to the document creation support apparatus 10 (interpretation workstation 3) and is saved in the storage unit 103.

In Step ST11, the image acquisition unit 11 acquires the diagnosis target image saved in the storage unit 103. In Step ST12, the feature portion extraction unit 12 extracts abnormal shadows as feature portions from the diagnosis target image acquired in Step ST11. In Step ST13, the feature portion analysis unit 13 analyzes the abnormal shadow extracted from the diagnosis target image, and specifies the classification and properties of the disease corresponding to the abnormal shadow.

In Step ST14, the relevant portion analysis unit 14 specifies the relevant portion related to the classification of the disease specified in Step ST13 based on the relevant portion table 30. In Step ST15, the relevant portion analysis unit 14 analyzes the relevant portion specified in Step ST14, and makes a determination on a predetermined determination item for the relevant portion. The relevant portion analysis unit 14 specifies a determination item based on the relevant portion table 30.

In Step ST16, the text generation unit 15 generates text including a description regarding the classification and properties of the disease corresponding to the abnormal shadow specified in Step ST13 and a description regarding the determination result for the relevant portion derived in Step ST15.

In Step ST17, the display control unit 16 performs control such that the text generated in Step ST16 is displayed on the display screen of the display unit 104. The user can use the text displayed on the display unit 104 as a part or all of a document (interpretation report) created by the user. The user can also add or modify the text displayed on the display unit 104.

As described above, with the document creation support apparatus 10 according to the embodiment of the disclosed technology, text generated based on the diagnosis target image includes not only a description regarding the classification of the disease corresponding to the abnormal shadow but also a description regarding the relevant portion related to the classification of the disease. That is, in the automatic generation of text based on an image, it is possible to include, in the text, a description of a portion other than the main onset portion of the disease described in the text. This makes it possible to effectively support the creation of a document (interpretation report) by the user.

In addition, as shown in FIG. 5, in the relevant portion table 30, the text describing the classification of the disease with which the relevant portion is not associated does not include the description regarding the relevant portion. That is, the text generation unit 15 includes, in the text, the description regarding the relevant portion in a case where the classification of the disease described in the text is a specific classification. In addition, the text generation unit 15 may include, in the text, the description regarding the relevant portion in a case where the classification of the disease described in the text is malignant (cancer). In other words, in a case where the classification of the disease described in the text is benign, the description regarding the relevant portion may not be included in the text. Further, in the present embodiment, the case where the description regarding properties of the abnormal shadow is included in the text is illustrated, but the description regarding properties of the abnormal shadow may not be included in the text.

Second Embodiment

FIG. 9 is a functional block diagram showing an example of a functional configuration of the document creation support apparatus 10 according to a second embodiment of the disclosed technology. The document creation support apparatus 10 according to the present embodiment is different from the document creation support apparatus 10 (see FIG. 3) according to the first embodiment described above in that it includes a designation reception unit 17 instead of the feature portion extraction unit 12.

The designation reception unit 17 receives the designation of the abnormal shadow (feature portion) included in the diagnosis target image. The abnormal shadow can be designated, for example, by the user clicking or dragging a partial region in the diagnosis target image displayed on the display screen of the display unit 104 using an input device such as a mouse.

The feature portion analysis unit 13 analyzes an abnormal shadow according to the designation received by the designation reception unit 17 and specifies the classification and properties of the disease corresponding to the abnormal shadow. The relevant portion analysis unit 14 specifies a relevant portion related to the classification of the disease specified by the feature portion analysis unit 13, and makes a determination on a predetermined determination item for the specified relevant portion.

The text generation unit 15 generates text including a description regarding the classification and properties of the disease corresponding to the abnormal shadow according to the designation received by the designation reception unit 17 and a description regarding the determination result for the relevant portion specified by the relevant portion analysis unit 14. The display control unit 16 performs control such that a plurality of pieces of text generated by the text generation unit 15 are displayed on the display unit 104.

With the document creation support apparatus according to the second embodiment of the disclosed technology, since the text is generated for the abnormal shadow (feature portion) designated by the user, it is possible to effectively support the creation of a document (interpretation report) by the user.

The document creation support apparatus may generate and display text as follows. For example, before receiving the designation of the abnormal shadow (feature portion) by the user, a plurality of pieces of text may be generated in advance for each of the plurality of abnormal shadows (feature portions). After that, in a case where an abnormal shadow (feature portion) is designated by the user, control may be performed such that text related to the designated abnormal shadow (feature portion) is selected from among a plurality of pieces of text generated in advance, and the selected text is displayed on the display unit 104. The displayed text includes a description regarding the relevant portion.

Further, as hardware structures of processing units that execute various kinds of processing such as each functional unit of the document creation support apparatus 10 according to the first and second embodiments described above, various processors shown below can be used. As described above, the various processors include a programmable logic device (PLD) as a processor of which the circuit configuration can be changed after manufacture, such as a field-programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example in which a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

The disclosure of JP2021-007429 filed on Jan. 20, 2021 is incorporated herein by reference in its entirety. Further, all literatures, patent applications, and technical standards described herein are incorporated by reference to the same extent as if the individual literatures, patent applications, and technical standards were specifically and individually stated to be incorporated by reference.

What is claimed is:

1. A document creation support apparatus comprising at least one processor and a memory storing a relevant portion table that associates classifications of diseases with corresponding relevant portions and with corresponding determination items for other diseases expected to occur in the relevant portions, wherein the processor is configured to:

generate text describing a classification of a disease for at least one feature portion included in an image;

specify, based on the relevant portion table, the relevant portion related to the classification of the disease described in the text;

analyze the specified relevant portion based on the determination item associated with the relevant portion in the table to obtain a determination result; and include, in the text, a description regarding the determination result for the specified relevant portion.

2. The document creation support apparatus according to claim 1, wherein the processor includes, in the text, the description regarding the relevant portion in a case where the classification of the disease described in the text is a specific classification.

3. The document creation support apparatus according to claim 1, wherein the processor includes, in the text, the description regarding the relevant portion in a case where the classification of the disease described in the text is malignant.

4. The document creation support apparatus according to claim 1, wherein the processor is configured to:

receive a designation of the feature portion; and include, in the text, the description regarding the relevant portion related to the classification of the disease corresponding to the designated feature portion.

5. A document creation support method in which at least one processor included in an information processing apparatus executes processing of:

storing, in a memory, a relevant portion table that associates classifications of diseases with corresponding relevant portions and with corresponding determination items for other diseases expected to occur in the relevant portions;

generating text describing a classification of a disease for at least one feature portion included in an image;

specifying, based on the relevant portion table, the relevant portion related to the classification of the disease described in the text;

analyzing the specified relevant portion based on the determination item associated with the relevant portion in the table to obtain a determination result; and including, in the text, a description regarding the deter-
mination result for the specified relevant portion.

6. A non-transitory computer-readable storage medium
storing a program for causing at least one processor included
in an information processing apparatus to execute processing of:

storing, in a memory, a relevant portion table that asso-
ciates classifications of diseases with corresponding
relevant portions and with corresponding determination
items for other diseases expected to occur in the
relevant portions;

generating text describing a classification of a disease for
at least one feature portion included in an image;

specifying, based on the relevant portion table, the rel-
evant portion related to the classification of the disease
described in the text;

analyzing the specified relevant portion based on the
determination item associated with the relevant portion
in the table to obtain a determination result; and including, in the text, a description regarding the determination result for the specified relevant portion.

\* \* \* \* \*